(12) United States Patent
Kim et al.

(10) Patent No.: US 11,763,955 B2
(45) Date of Patent: Sep. 19, 2023

(54) METHOD OF PRODUCING TC-99M BY USING NUCLEAR RESONANCE FLUORESCENCE

(71) Applicant: KOREA HYDRO & NUCLEAR POWER CO., LTD., Gyeongsangbuk-do (KR)

(72) Inventors: Yonghee Kim, Daejeon (KR); Jiyoung Lee, Daejeon (KR); Seongdong Jang, Daejeon (KR); Ur Rehman Haseeb, Daejeon (KR); Eun Ki Lee, Daejeon (KR); Young Ae Kim, Daejeon (KR); Ji Eun Jung, Daejeon (KR)

(73) Assignee: Korea Hydro & Nuclear Power Co., Ltd., Gyeongsangbuk-do (KR)

( * ) Notice: Subject to any disclaimer, the term of this patent is extended or adjusted under 35 U.S.C. 154(b) by 471 days.

(21) Appl. No.: 16/647,669

(22) PCT Filed: Sep. 18, 2017

(86) PCT No.: PCT/KR2017/010190
§ 371 (c)(1),
(2) Date: Mar. 16, 2020

(87) PCT Pub. No.: WO2019/054539
PCT Pub. Date: Mar. 21, 2019

(65) Prior Publication Data
US 2020/0234837 A1 Jul. 23, 2020

(30) Foreign Application Priority Data
Sep. 18, 2017 (KR) .................. 10-2017-0119251

(51) Int. Cl.
*G21G 1/00* (2006.01)
*A61K 51/02* (2006.01)

(52) U.S. Cl.
CPC ........... *G21G 1/001* (2013.01); *A61K 51/025* (2013.01); *G21G 2001/0042* (2013.01)

(58) Field of Classification Search
CPC .................................. G21G 1/00; A61K 51/02
See application file for complete search history.

(56) References Cited

U.S. PATENT DOCUMENTS

| 9,576,692 B2 | 2/2017 | Baurichter et al. |
| 2002/0169351 A1 | 11/2002 | Brown |
| 2014/0029710 A1 | 1/2014 | Wilson et al. |
| 2014/0294135 A1 | 10/2014 | Allenou et al. |

FOREIGN PATENT DOCUMENTS

| JP | 2011092102 A | 2/2012 |
| JP | 2012242164 A | 12/2012 |

OTHER PUBLICATIONS

Daniel Robert Lowe, Novel Production Techniques of Radioisotopes Using Electron Accelerators, UNLV Theses Dissertation. (Year: 2012).*
D. Habs. U. Koster, Production of medical radioisotopes with high specific activity in photonuclear reactions with γ-beams of high intensity and large brilliance, Appl Phys B 103, 501-519. (Year: 2011).*
Tatsuhiko Ogawa et al, Development of general nuclear resonance fluoresecence model, J Nucl Sci and Tech, 53(11), 1766-1773. (Year: 2016).*
Hiroyasu Ejiri et al. Resonant Photonuclear Reactioins for Isotope Transmutation, J of Physical Society of Japan, 80, 094202. (Year: 2011).*
Kim, Y., Producing 99mTc with Photo-Nuclear Reaction, MIT-KAIST Symposium, Mar. 30, 2017.
Lee, J. et al., A Physics Study on Photoproduction of Tc-99m Using the NRF Phenomenon, Transcations of the Korean Nuclear Society Spring Meeting, May 18-19, 2017.

* cited by examiner

*Primary Examiner* — Michael G. Hartley
*Assistant Examiner* — Jagadishwar R Samala
(74) *Attorney, Agent, or Firm* — Standley Law Group LLP; James L. Kwak; Kenny W. Pung

(57) ABSTRACT

Disclosed is a method of producing Tc-99m by using nuclear resonance fluorescence. More specifically, and a method of preparing Tc-99m by using nuclear resonance fluorescence includes irradiating a ground-state Tc-99 nucleus with a photon beam, thereby causing a nuclear transmutation to proceed such that the nucleus excited to high energy and then undergoes a transition to Tc-99m.

4 Claims, 7 Drawing Sheets

| Elevel (keV) | Cross-section (eVb) | Ix | Final level | BR | BR to 143 keV | Total BR |
|---|---|---|---|---|---|---|
| 509.096 | 0.2580847 | 100 | 143 | 100.0% | 100.0% | 100.0% |
| 534.43 | 1021.236 | 100 | 143 | 100.0% | 100.0% | 100.0% |
| 612.37 | 0.01739054 | 7.7 | 509 | 7.1% | 7.1% | 100.0% |
|  |  | 100 | 143 | 92.9% | 92.9% |  |
| 671.478 | 1,884.78 | 21 | 509 | 10.4% | 10.4% | 59.9% |
|  |  | 81 | 181 |  |  |  |
|  |  | 100 | 143 | 49.5% | 49.5% |  |
| 884.259 | 3,874.083 | 86.3 | 671 | 31.0% | 18.6% | 57.3% |
|  |  | 100 | 612 | 35.9% | 35.9% |  |
|  |  | 7.8 | 509 | 2.8% | 2.8% |  |
|  |  | 41.2 | 181 |  |  |  |
|  |  | 43.1 | 140 |  |  |  |
| 920.579 | 0.001689 | 0.16 | 761 |  |  | 26.1% |
|  |  | 0.02 | 671 | 0.0% | 0.0% |  |
|  |  | 0.12 | 509 | 0.1% | 0.1% |  |
|  |  | 100 | 181 |  |  |  |
|  |  | 35.3 | 143 | 26.0% | 26.0% |  |
| 986.17 | 88.35888 | 16.7 | 719 |  |  | 60.2% |
|  |  | 100 | 612 | 52.4% | 52.4% |  |
|  |  | 14.8 | 509 | 7.8% | 7.8% |  |
|  |  | 40.7 | 181 |  |  |  |
|  |  | 18.5 | 140 |  |  |  |
| 1004.068 | 0.01187832 | 1.1 | 761 |  |  | 6.6% |
|  |  | 2.1 | 534 | 1.9% | 1.9% |  |
|  |  | 100 | 181 |  |  |  |
|  |  | 5 | 143 | 4.6% | 4.6% |  |
| 1072.23 | 5.843238 | 100 | 534 | 100.0% | 100.0% | 100.0% |
| 1129.105 | 0.2255207 | 100 | 671 | 64.9% | 38.9% | 74.0% |
|  |  | 34 | 509 | 22.1% | 22.1% |  |
|  |  | 20 | 143 | 13.0% | 13.0% |  |
| 1,135.04 | 2,043.462 | 20 | 884 | 11.1% | 6.4% | 81.4% |
|  |  | 100 | 612 | 55.6% | 55.6% |  |
|  |  | 35 | 509 | 19.4% | 19.4% |  |
|  |  | 25 | 181 |  |  |  |

FIG. 6

| E_level (keV) | Cross-section (eVb) | I_x | Final level | BR | BR to 143 keV | Total BR |
|---|---|---|---|---|---|---|
| 1,176.48 | 39,464.84 | 3.7 | 986 | 3.2% | 1.9% | 88.2% |
| | | 12.2 | 739 | | | |
| | | 100 | 612 | 86.3% | 86.3% | |
| 1,198.89 | 5,476.068 | 39 | 509 | 20.0% | 20.0% | 71.3% |
| | | 56 | 181 | | | |
| | | 100 | 143 | 51.3% | 51.3% | |
| 1,207.26 | 1,5870.1 | 100 | 884 | 29.6% | 16.9% | 33.0% |
| | | 90.5 | 671 | 26.8% | 16.0% | |
| | | 19.1 | 625 | | | |
| | | 66.7 | 181 | | | |
| | | 61.9 | 0 | | | |
| 1,320.732 | 0.9862262 | 68.8 | 612 | 40.8% | 40.8% | 100.0% |
| | | 100 | 509 | 59.2% | 59.2% | |
| 1,329.404 | 31,875.37 | 100 | 719 | | | 31.8% |
| | | 93.3 | 612 | 31.8% | 31.8% | |
| | | 100 | 140 | | | |
| 1,405.454 | 0.4388057 | 100 | 671 | 71.4% | 42.8% | 71.4% |
| | | 40 | 509 | 28.6% | 28.6% | |
| 1,444.134 | 3,089.747 | 38.5 | 612 | 20.8% | 20.8% | 45.9% |
| | | 46.2 | 509 | 25.0% | 25.0% | |
| | | 100 | 181 | | | |
| ~~1,494.15~~ | 0.01187832 | 57.1 | 986 | 23.5% | 14.2% | 34.4% |
| | | 85.7 | 884 | 35.3% | 20.2% | |
| | | 100 | 140 | | | |
| ~~1,543.22~~ | 0.01187832 | 100 | 1,176 | 100.0% | 88.2% | 88.2% |

FIG. 7

METHOD OF PRODUCING TC-99M BY USING NUCLEAR RESONANCE FLUORESCENCE

TECHNICAL FIELD

The present invention relates to a method of producing Tc-99m by using nuclear resonance fluorescence.

STATEMENT REGARDING PRIOR DISCLOSURES BY THE INVENTORS

The invention was first published in MIT-KAIST Symposium on 30 Mar. 2017 (30 Mar. 2017).

The invention was also published in Transactions of the Korean Nuclear Society Spring Meeting on 18 May 2017 (18 May 2017).

BACKGROUND ART

Tc-99 is an important radioisotope and may be beneficial or harmful to humans depending on a state thereof. Ground-state $^{99}$Tc is produced in nuclear reactors and accounts for about 0.1% of total spent fuel material. In particular, $^{99}$Tc has a very long half-life of 211,000 years and a high level of toxicity, thereby causing many difficulties in disposal thereof.

Technetium-99m (Tc-99m) emits gamma rays of 142.6 keV and has a relatively short half-life of 6 hours so as to be widely used in nuclear medicine for diagnoses of heart disease, cancer, stroke, and the like. After injecting Tc-99m into a human body, a path of the active area may be medically analyzed through gamma rays, whereby diseases may be easily diagnosed and, at the same time, there is an advantage that the patient's exposure to Tc-99m is low. Accordingly, demands for Tc-99m are increasing every year. However, Tc-99m is an isotope having a short half-life and produced artificially, and thus it is difficult to meet supply demands.

Production of Tc-99m is typically classified into direct production and indirect production.

The direct production is a method of producing Tc-99m from a decay process after producing molybdenum-99 (Mo-99) by irradiating molybdenum-98 (Mo-98) with neutrons mainly inside the reactor. Alternatively, there is also a method of producing Tc-99m through $^{100}$Mo(p,2n)$^{99m}$Tc reaction by irradiating molybdenum-100 (Mo-100) with protons. Because Tc-99m has characteristics of short half-life (should be used right after the production), this method has a drawback in which transportation cost from production facilities to medical sites is the biggest problem, and production efficiency is low.

The indirect production is a method of separating and purifying Mo-99 produced from nuclear reactor fission reaction mainly inside the reactor. Mo-99, a parent nuclide of Tc-99m, has a relatively long half-life of 2.7489 days, making transportation to a medical site relatively easy. Once transported to the medical site in a form of Mo-99, Tc-99m may be produced at the site by β decay. The indirect production method has advantages in terms of transportation than the direct production method, but efficiency thereof is not high as Mo-99 is to be produced and refined in the research reactor and the like, whereby it is difficult to produce Tc-99m on a large scale to meet demand.

DOCUMENTS OF RELATED ART

Patent Document

Korean Patent Application Publication No. 10-2014-0050597 (Apr. 29, 2014)

DISCLOSURE

Technical Problem

Accordingly, the present invention relates to a new method of producing Tc-99m and is to provide a method of producing Tc-99m using Tc-99 which is nuclear waste.

Technical Solution

In order to accomplish the above object, there is provided a method of producing Tc-99m by using nuclear resonance fluorescence according to the present invention, the method including: irradiating a ground-state Tc-99 nucleus with a photon beam, thereby causing a nuclear transmutation to proceed such that the nucleus is excited to high energy and then undergoes a transition to Tc-99m.

Preferably, the photon beam may be a gamma ray produced by laser Compton scattering, more preferably, the energy of the gamma ray may be any one of energy levels of no less than 142 keV of a Tc-99 nucleus, and still more preferably, the Tc-99 nucleus may be repeatedly irradiated with the gamma rays having two energies different from each other among the energy levels of the Tc-99 nucleus.

Advantageous Effects

As described above, the method of producing Tc-99m according to the present invention is performed by a nuclear transmutation in which, a Tc-99 nucleus of a ground state is irradiated with a photon beam, whereby the nucleus is excited to high energy by a nuclear resonance fluorescence reaction and then undergoes a transition to the ground state. Accordingly, the producing method above has an advantage in which the $^{99m}$Tc can be produced using $^{99}$Tc having a long half-life and high level of radioactivity.

DESCRIPTION OF DRAWINGS

FIGS. 6 and 7 are diagrams showing data related to transition at each energy level of the Tc-99 nucleus.

BEST MODE

Specific structures or functional descriptions presented in the embodiments of the present invention are only illustrated for the purpose of describing the embodiments according to the concept of the present invention, and the embodiments according to the concept of the present invention may be implemented in various forms. In addition, the present invention should not be construed as limited to the embodiments described herein but should be understood to include all modifications, equivalents, and substitutes included in the spirit and scope thereof.

The present invention corresponds to a new method of producing Tc-99m and irradiates Tc-99 with a photon beam generated by laser Compton scattering (LCS) to cause a nuclear resonance fluorescence (NRF) reaction, thereby producing Tc-99m.

That is, it is a method of producing Tc-99m by a nuclear transmutation in which, when a Tc-99 nucleus of the ground state is irradiated with the LCS photon beam of specific energy, the Tc-99 nucleus is excited to high energy by an NRF reaction, and then undergoes a transition to a Tc-99m nucleus.

Tc-99 is a radioactive isotope that undergoes R decay and has a half-life of 211,100 years. Naturally, trace amounts of Tc-99 exist due to spontaneous fission of uranium, but artificially, Tc-99 is produced at a high rate annually as fission products. When Tc-99m is produced by an NRF nuclear method using the LCS, it may be directly produced from Tc-99, which has already abundantly artificially been produced. Meanwhile, the Tc-99 element is stable, there is no problem in transportation, and a Tc-99m production facility is simple. Therefore, transportation and utilization problems are solved, whereby Tc-99m of low-cost may be supplied.

Photoexcitation of the NRF (Nuclear Resonance Fluorescence)

Figure 1:
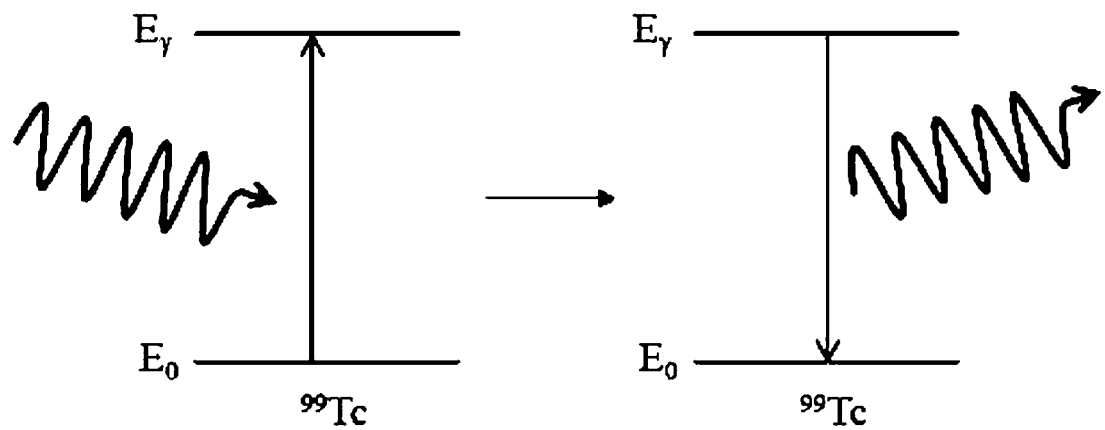
FIG. 1 schematically shows an NRF reaction.

The NRF reaction is a result of absorption of a nucleus and a release of high energy photons arising from the absorption of the nucleus, and FIG. 1 schematically shows the NRF reaction, with $E_0$ and $E_\gamma$ representing the energy of the ground and excited states of the nucleus, respectively. The ground-state $^{99}$Tc nucleus may be excited by a photon with an energy of approximately $E_\gamma$, and an excited-state $^{99}$Tc nucleus lasts for a very short time (~ femto seconds) and emits photons, thereby decaying back to the ground state.

An NRF cross section follows a Breit-Wigner formula and is shown in [Equation 1] below.

$$\sigma(E) = \frac{1}{4\pi} \frac{2J+1}{2(J_0+1)} \left(\frac{hc}{E}\right)^2 \frac{\Gamma \Gamma_0}{(E-E_r)^2 + \Gamma^2/4} \quad \text{[Equation 1]}$$

In above equation, J is spin of the excited state, $J_0$ is spin of the ground state, $\Gamma$ is total damping width of all damping widths from an excitation energy level, $\Gamma_0$ is partial damping width from the excited state to the ground state, and E is incident gamma ray energy, and $E_\gamma$ is energy level of the excited state. Data for $^{99}$Tc was based on the Evaluated Nuclear Structure Data File (ENSDF), and the NRF cross section was calculated by the Particle and Heavy Ion Transport code System (PH ITS).

Figure 2:
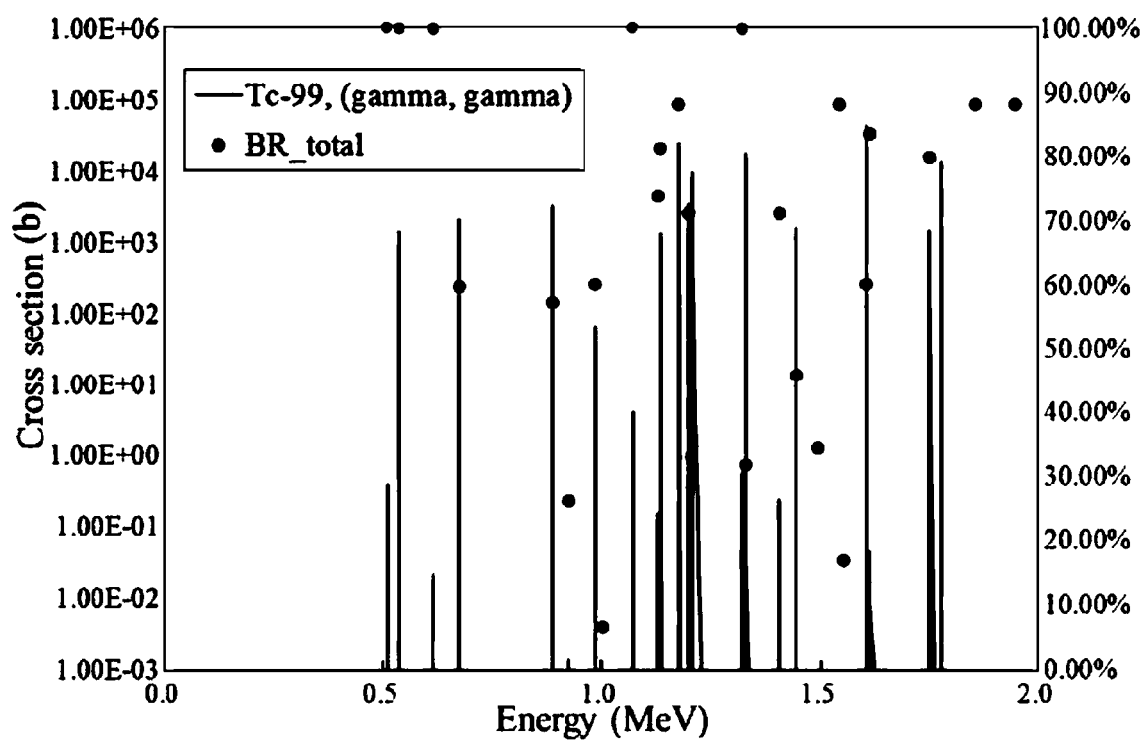
FIG. 2 is a graph showing an NRF cross section and a $BR_{total}$ at each of corresponding excitation energy levels enabling generation of Tc-99m.

FIG. 2 is a graph showing an NRF cross section and a $BR_{total}$ at each of corresponding excitation energy levels enabling generation of Tc-99m. The $BR_{total}$ means a branching ratio to Tc-99m at a corresponding excitation energy level, and when information on a photon branching ratio for each level deduced from isomer transition decay is missing in the ENSDF file, the $BR_{total}$ is unable to be calculated for the corresponding level even though a branching ratio to $^{99m}$Tc exists at the corresponding level. When the ENSDF file does not have a transition path to the ground state for each of the excitation energies, errors may occur for some of the cross sections. In FIG. 2, the $BR_{total}$ or the cross section in the case described above is not indicated.

The NRF cross section in a state of the nuclear isomer is so small, approximately $10^{-13}$ b, not indicated in FIG. 2, that direct excitation of Tc-99 of the ground state to an energy level of Tc-99m is impossible. Accordingly, indirect excitation using different energy levels should be considered. It is also important to understand that an NRF cross section peak is sharp and narrow. In addition, full width at half maximum (FWHM) occurs at an energy of approximately 2-3 eV. The cross section is proportional to transition strength, so accurate measurement is essential. It should be noted that uncertainty of a current cross section prediction value is considered very high, for example, the actual cross section may be between $1/100$ and 100 times a measured value.

LCS (Laser Compton Scattering) Gamma Rays

Figure 3:
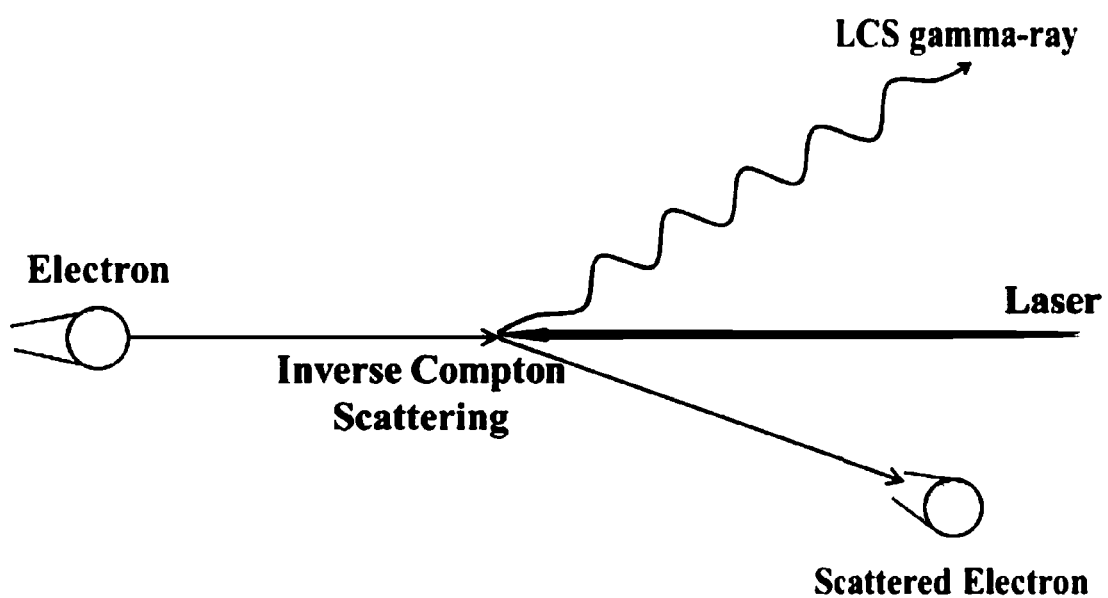
FIG. 3 is a view conceptually showing an LCS phenomenon.

Photonuclear excitation may occur using high luminance gamma rays generated from LCS interactions. Meanwhile, an LCS phenomenon refers to an increase in energy of a photon (that is, a wavelength is shortened) due to elastic scattering between a low energy laser photon and a high energy electron and may be approximately illustrated as shown in FIG. 3.

Because LCS gamma rays are energy-tunable, are quasi-monochromatic light, and have beam-like properties, the LCS gamma rays may be used for photonuclear excitation. For efficiency and high nuclear excitation rate, intensity of the LCS gamma rays is to be strong enough.

In the present embodiment, an LCS facility using an energy-recovery LINAC (ERL) was used as a gamma ray source. Recently, T. Hayakawa et al. designed a high-flux LCS gamma ray facility using a 350 MeV ERL system, and it is reported the facility generates $10^{13}$ gamma rays per second.

Figure 4:
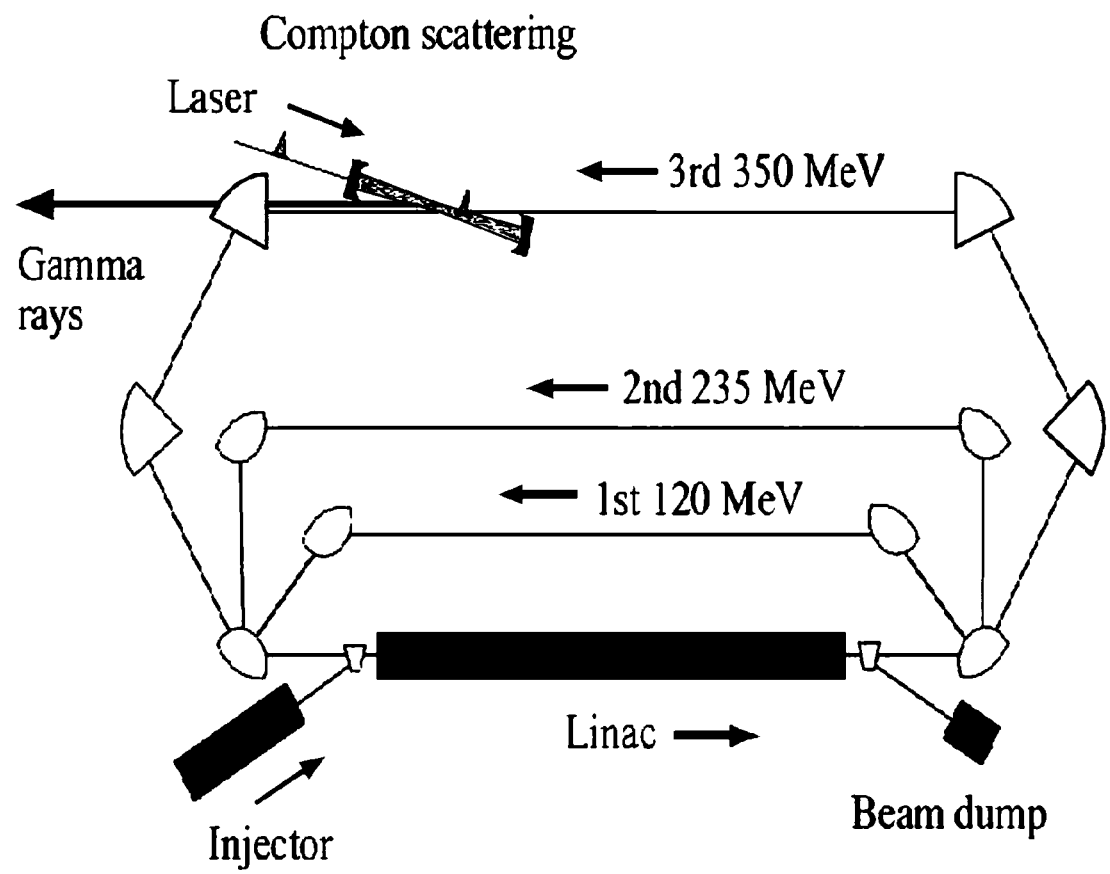
FIG. 4 is a block diagram showing an LCS gamma ray facility using an ERL system.

FIG. 4 is a block diagram showing an LCS gamma ray facility using an ERL system of Hayakawa, and the facility employs three loop designs for cost reduction and miniaturization. The electron beam emitted from an injector is accelerated by the superconducting LINAC. After third recycling by passing through the three loops, the electron beam is reinjected into the LINAC with a decelerated status and electron energy is fed back into the high frequency cavity of the superconducting LINAC. The LCS gamma rays are finally generated by collisions of electrons and laser photons at an end part of a third loop. Table 1 below shows the main design parameters. Table 1 below shows the main design parameters.

TABLE 1

| Design parameter | Value |
| --- | --- |
| Electron energy | 350 MeV |
| Laser wavelength | 1064 nm |
| Electron-beam-induced current | 100 mA |
| Average laser output power | ~100 W |
| Electron bundle charge | 1 nC |
| Pulse energy | 1.80 μJ |
| Laser super cavity | 3000 |

Photogeneration of $^{99m}$TC

The photonuclear reaction ratio ($N_{reac}$) may be calculated using the NRF cross section and an LCS spectrum and is as shown in [Equation 2] below.

$$N_{reac} = n_{target} BR_{total} \int_{E_l}^{E_h} \sigma_{NRF} dE_\gamma \frac{dN_\gamma}{dE_\gamma} \int_0^d e^{-\Sigma_{NRF} x} dx \quad \text{[Equation 2]}$$

Here, $n_{target}$ is number of atoms per unit cubic centimeter of target material, d is thickness of the target material, $\sigma_{NRF}$ is an NRF-based resonance cross section, and $E_l$ and $E_h$ are lowest and highest energies of the LCS gamma ray photon spectrum, respectively. $\Sigma_{NRF}$ is a macroscopic NRF cross section and is a product of $\sigma_{NRF}$ and $Nn_{target}$, and $dN_\gamma/dE_\gamma$ is a spectral density calculated from [Equation 3] below.

$$\frac{dN_\gamma}{dE_\gamma} = \frac{N_\gamma}{\sigma_i} \int_{E_0-\sigma_E}^{E_0+\sigma_E} \frac{d\sigma}{dE_\gamma} \frac{1}{\sqrt{2\pi}\delta_E} \exp\left[-\frac{(E_e - E_0)^2}{2\delta_E^2}\right] dE_e \quad \text{[Equation 3]}$$

Here, $dN_\gamma$ is total gamma ray intensity of a facility in a unit of #/sec, $\sigma_t$ is a total Compton scattering cross section in mb, $d\sigma/dE_\gamma$ is the differential Compton scattering cross section in a unit of mb/MeV, $E_0$ is central electron beam energy in a unit of MeV, and $\delta^2_E$ represents a variance of a central electron beam energy value.

In [Equation 2], gamma ray attenuation in a target region is considered, and some of $\sigma_{NRF}$ are so large to greatly affect the gamma ray attenuation. The spectral density is assumed to be constant because it is less than 10 eV in an energy range between $E_l$ and $E_h$.

Figure 5:
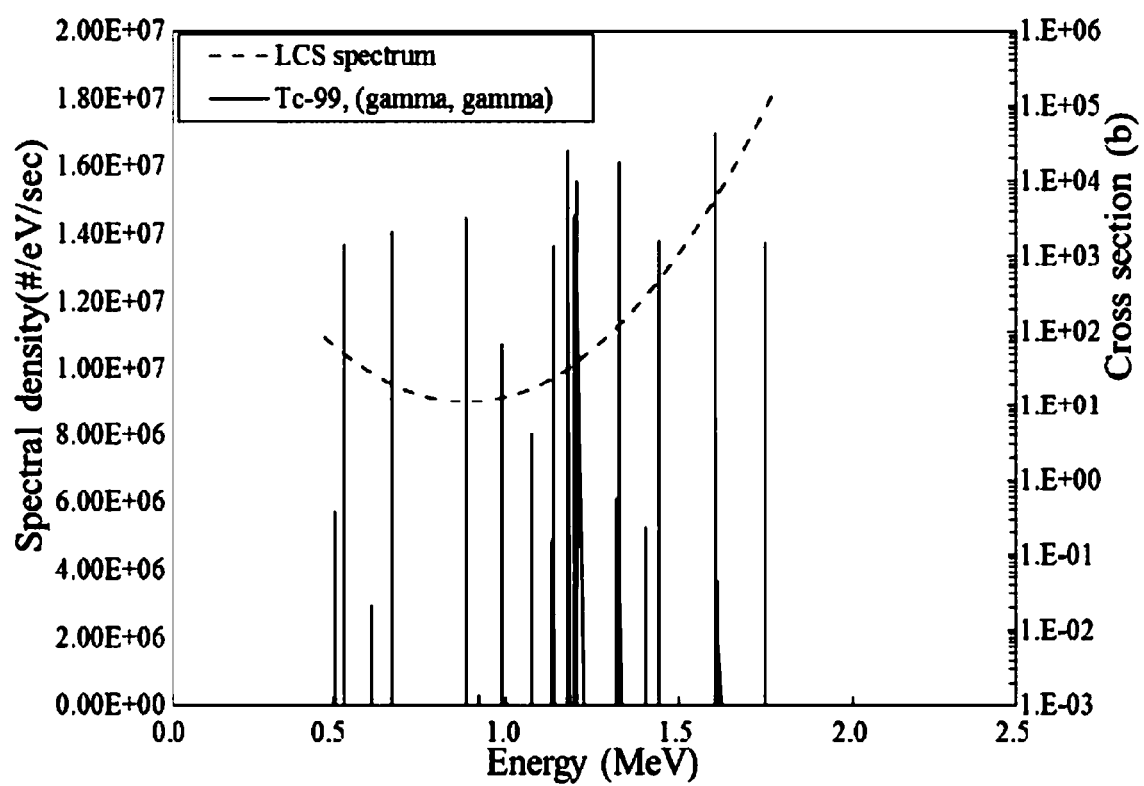
FIG. 5 is a graph showing LCS spectra and $^{99}$Tc NRF cross sections.

Electron energy designed in the ERL facility shown in FIG. 4 is 350 MeV, but as required LCS photon energy is reduced, the electron energy is reduced from 350 MeV to 315 MeV. Here, maximum LCS energy is adjusted to 1.77 MeV, because, in energy no less than 1.77 MeV, the NRF cross section is very small and much information is missing. Intensity of a corresponding LCS photon is $2.1 \times 10^{13}$ γ/s, and by using the LCS gamma ray of such intensity, the spectrum of the LCS photon was optimized as shown in FIG. 5. The photonuclear reaction ratio was calculated to be $6.64 \times 10^{10}$/sec.

Nuclear activity according to the reaction ratio described above is calculated by [Equation 4].

[Equation 4]

$$A = N_{reac}(1 - e^{-in2/T_{1/2} \times t})$$

TABLE 2

| Irradiation time (hr) | 0.5 | 1 | 3 | 6 | 12 | 30 |
|---|---|---|---|---|---|---|
| Nuclear activity (mCi) | 0.2 | 0.3 | 0.9 | 1.5 | 2.3 | 2.9 |

FIGS. 6 and 7 are diagrams showing data related to transition at each energy level of the Tc-99 nucleus, wherein the Tc-99 nucleus has various energy levels. In FIGS. 6 and 7, the "$E_{level}$" represents the quantized energy level of Tc-99, and the "Cross section" represents the nuclear reaction cross section of the NRF reaction in which the Tc-99 nucleus reaches the "$E_{level}$" from the ground state. The "$I_\gamma$" represents the branching ratio of the transition of nuclear isomers, and the "Final level" represents the energy level to which the excited nucleus undergoes a transition. The "BR" represents the branching ratio from "$E_{level}$" to the "Final level", and the "BR to 143 keV" represents the branching ratio at which the Tc-99 nucleus finally reaches Tc-99m. The "Total BR" is the branching ratio at which the Tc-99 nucleus of "$E_{level}$" finally reaches Tc-99m and is equal to the sum of all the "BR to 143 keV" at that "$E_{level}$". When the "Final level" does not have a branching ratio reaching Tc-99m, that is, when the value of the "BR to 143 keV" is 0, a "BR" field is blank and a "BR" field is blank even when the "BR" is unable to be calculated because of no "$I_\gamma$" information in the ENSDF file.

Figure 8:
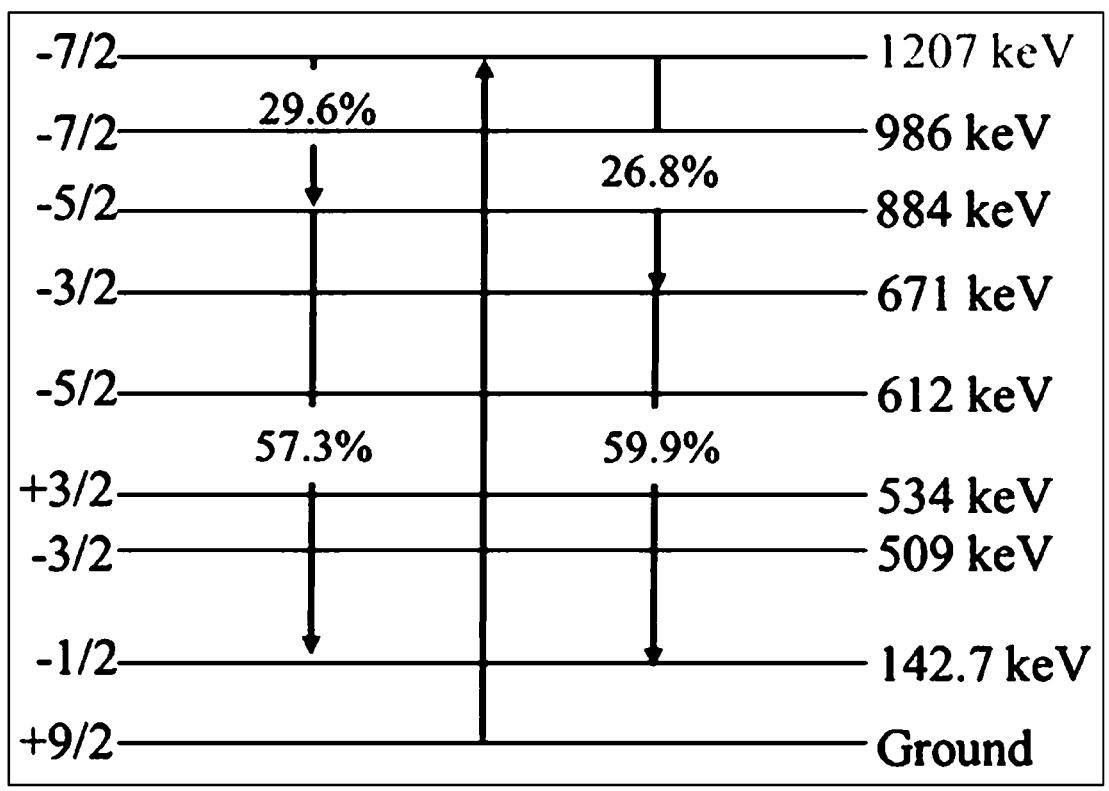
FIG. 8 is a view showing a transition process of a Tc-99 nucleus excited by specific energy 1,207 keV to a Tc-99m nucleus.

FIG. 8 is a view showing a transition process of a Tc-99 nucleus excited by specific energy 1,207 keV to a Tc-99m nucleus and shows an energy level according to each spin of the nucleus when the Tc-99 nucleus excited at 1,207 keV undergoes a transition to Tc-99m. The left side shows spin values representing total angular momenta, and the right side shows the corresponding quantized energy levels. The Tc-99 nucleus is excited to 1,207 keV and then undergoes a transition in two directions of 884 keV and 671 keV with a probability of 29.6% and 26.8%, respectively. Tc-99 undergoes a transition to Tc-99m at an energy level of 884 keV with a probability of 57.3% and undergoes a transition to Tc-99m at an energy level of 671 keV with a probability of 59.9%.

Thus, the Tc-99 nucleus is excited to 1,207 keV and then undergoes a transition to Tc-99m with a total probability of 33%. In other words, when the Tc-99 nucleus is irradiated with a 1,207 keV LCS photon beam, Tc-99m may be produced with a probability of 33% with respect to the excited nucleus. Such efficiency is very high compared to efficiency of current methodologies. Further, by repeatedly irradiating the same target with multiple LCS photon beams each having, that is, 1,176 keV, 1,207 keV, 1,329 keV, and 1,604 keV, the efficiency may be further increased.

As described above, the present invention may produce $^{99m}$Tc, an isotope for medical use, by recycling $^{99}$Tc on the basis of the nuclear resonance fluorescence, and also solve the problem of disposing of nuclear waste by recycling $^{99}$Tc which is a radioisotope having a long half-life.

The present invention described above is not limited to the above-described embodiments and the accompanying drawings, and it will be apparent to those skilled in the art that various substitutions, modifications, and changes may be made without departing from the spirit of the present invention.

The invention claimed is:

1. A method of producing Tc-99m by using nuclear resonance fluorescence, the method comprising:
   irradiating a ground-state Tc-99 nucleus with a photon beam, thereby causing a nuclear transmutation to proceed such that the nucleus is excited to high energy and then undergoes a transition to Tc-99m.

2. The method of producing Tc-99m of claim 1, wherein the photon beam is a gamma ray produced by laser Compton scattering.

3. The method of producing Tc-99m of claim 2, wherein the energy of the gamma ray is any one of energy levels of no less than 142 keV of a Tc-99 nucleus.

4. The method of producing Tc-99m of claim 3, wherein the Tc-99 nucleus is repeatedly irradiated with the gamma rays having two energies different from each other among the energy levels of the Tc-99 nucleus.

* * * * *

UNITED STATES PATENT AND TRADEMARK OFFICE
CERTIFICATE OF CORRECTION

| | |
|---|---|
| PATENT NO. | : 11,763,955 B2 |
| APPLICATION NO. | : 16/647669 |
| DATED | : September 19, 2023 |
| INVENTOR(S) | : Yonghee Kim et al. |

It is certified that error appears in the above-identified patent and that said Letters Patent is hereby corrected as shown below:

In the Specification

Column 3, Line 19, please delete "R" and insert -- β --.

Signed and Sealed this
Fourteenth Day of November, 2023

Katherine Kelly Vidal
*Director of the United States Patent and Trademark Office*